US010542925B2

(12) United States Patent
Kirenko et al.

(10) Patent No.: US 10,542,925 B2
(45) Date of Patent: Jan. 28, 2020

(54) DEVICE AND METHOD FOR MONITORING VITAL SIGNS

(71) Applicant: KONINKLIJKE PHILIPS N.V., Eindhoven (NL)

(72) Inventors: Ihor Olehovych Kirenko, Eindhoven (NL); Adriaan Johan Van Leest, Eindhoven (NL); Gerard De Haan, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 125 days.

(21) Appl. No.: 14/379,823

(22) PCT Filed: Feb. 21, 2013

(86) PCT No.: PCT/IB2013/051402
§ 371 (c)(1),
(2) Date: Aug. 20, 2014

(87) PCT Pub. No.: WO2013/128345
PCT Pub. Date: Sep. 6, 2013

(65) Prior Publication Data
US 2016/0015308 A1 Jan. 21, 2016

Related U.S. Application Data

(60) Provisional application No. 61/603,996, filed on Feb. 28, 2012.

(51) Int. Cl.
*A61B 5/00* (2006.01)
*A61B 5/22* (2006.01)
(Continued)

(52) U.S. Cl.
CPC ............ *A61B 5/222* (2013.01); *A61B 5/0013* (2013.01); *A61B 5/0059* (2013.01);
(Continued)

(58) Field of Classification Search
CPC ..... A61B 5/222; A61B 5/7289; A61B 5/0013; A61B 5/721; A61B 5/725; A61B 5/7278;
(Continued)

(56) References Cited

U.S. PATENT DOCUMENTS

2005/0075577 A1 4/2005 Chen
2007/0219059 A1* 9/2007 Schwartz ............ A61B 5/0205
482/8
(Continued)

FOREIGN PATENT DOCUMENTS

CN 101034308 A 9/2007
EP 1908401 A1 4/2008
(Continued)

OTHER PUBLICATIONS

Sun et al., "Motion-compensated noncontact imaging photoplethysmography to monitor cardiorespiratory status during exercise", Journal of Biomedical Optics, vol. 16[7], 077010, Jul. 2011.*
(Continued)

*Primary Examiner* — Carl H Layno
*Assistant Examiner* — Michael J Lau

(57) ABSTRACT

The present invention relates to a device and method for monitoring vital signs of a subject. In particular, the device for monitoring vital signs comprises, an imaging unit for obtaining image data of said subject, an interface for receiving motion data of said subject and/or said imaging unit, a processing unit for extracting vital signs of said subject from said image data, and a control unit for adapting parameters of said imaging unit and/or said processing unit based on the received motion data. A further aspect of the invention relates to a fitness device comprising a device for monitoring vital signs and a motion detection unit for providing said device for monitoring vital signs with motion data.

17 Claims, 5 Drawing Sheets

(51) Int. Cl.
*A61B 5/024* (2006.01)
*A61B 5/0205* (2006.01)
*A61B 5/11* (2006.01)

(52) U.S. Cl.
CPC ........ *A61B 5/0205* (2013.01); *A61B 5/02416* (2013.01); *A61B 5/721* (2013.01); *A61B 5/725* (2013.01); *A61B 5/7278* (2013.01); *A61B 5/7289* (2013.01); *A61B 5/1123* (2013.01); *A61B 5/1128* (2013.01); *A61B 2576/00* (2013.01)

(58) Field of Classification Search
CPC ... A61B 5/0059; A61B 5/0205; A61B 5/1123; A61B 2576/00; A61B 5/1128; A61B 5/02416
USPC ...... 328/128; 600/300, 301, 481; 482/54, 57
See application file for complete search history.

(56) References Cited

U.S. PATENT DOCUMENTS

| | | | |
|---|---|---|---|
| 2008/0161653 A1* | 7/2008 | Lin | A61B 5/0833 600/300 |
| 2008/0221399 A1* | 9/2008 | Zhou | A61B 5/021 600/301 |
| 2009/0141124 A1 | 6/2009 | Liu | |
| 2010/0305418 A1* | 12/2010 | Deliwala | A61B 5/14551 600/324 |
| 2011/0066007 A1* | 3/2011 | Banet | A61B 5/0402 600/301 |
| 2011/0066041 A1* | 3/2011 | Pandia | A61B 5/029 600/484 |
| 2011/0066381 A1 | 3/2011 | Garudadari | |
| 2011/0251493 A1* | 10/2011 | Poh | G06K 9/624 600/477 |
| 2011/0311119 A1* | 12/2011 | Jeanne | G06T 7/20 382/128 |
| 2012/0010478 A1* | 1/2012 | Kinnunen | A61B 5/02405 600/301 |

FOREIGN PATENT DOCUMENTS

| | | | |
|---|---|---|---|
| EP | 2116183 A1 | 11/2009 | |
| NL | WO2011/042858 A1 * | 4/2011 | ............... G06T 7/20 |
| WO | WO2009071128 A1 | 6/2009 | |
| WO | WO2010100594 A2 | 9/2010 | |
| WO | WO2011021128 A2 | 2/2011 | |
| WO | 2011042858 A1 | 4/2011 | |

OTHER PUBLICATIONS

Schmitz, G.L.L.H., "Video Camera based Photoplethysmography using Ambient Light", Graduation Symposium at Technical University of Eindhoven, Jan. 18, 2011, Eindhoven University of Technology (TUE). Dep. of Electrical Engineering, http://alexandria.tue.nl/extra2/afstversl/E/campusonly/710886.pdf.

* cited by examiner

DEVICE AND METHOD FOR MONITORING VITAL SIGNS

FIELD OF THE INVENTION

The present invention relates to a device and a method for monitoring vital signs of a subject, in particular for contactless or remote monitoring of vital signs.

BACKGROUND OF THE INVENTION

Classical methods of measuring biometrical signals or vital signs, such as heart rate, respiratory rate or blood oxygen saturation, require the user to wear annoying body sensors, which might be experienced as obtrusive to normal human life activity.

One solution to this problem is photoplethysmography imaging (PPG) which allows remote contactless monitoring of vital signs. PPG is based on the principle that temporal variations in blood volume in the skin lead to variations in light absorptions by the skin. Such variations can be registered by a video camera that takes images of an area of bare skin, for example the face. By looking at periodic variations of the intensity signal, e.g. the RGB values of a group of pixels from the video camera, the heart rate and respiratory rate can be extracted. However, as this method evaluates light coming from the target, any change in illumination conditions or a movement of the subject will create additional disturbances in a temporal signal. Such a disturbance signal can be measured by means of dedicated video processing algorithms applied to the video stream from a vital signs camera. The paper by Schmitz "Video Camera based Photoplethysmography using Ambient Light" (Graduation Symposium at the Technical University of Eindhoven, 2011), suggests that motion vectors can be used to track pixels containing heart rate information.

However, the measurement of a disturbance signal requires complex algorithms and increases the hardware requirements of a vital signs camera, such as higher resolution or better sharpness with the associated high-quality optics. Moreover, such video-based motion estimation and tracking in a high resolution video stream requires extensive signal processing with costly hardware.

SUMMARY OF THE INVENTION

It is an object of the present invention to provide a device and a method for reliable vital signs monitoring at reduced system costs.

In a first aspect of the present invention, a device for monitoring vital signs is presented that comprises an imaging unit for obtaining image data of said subject, an interface for receiving motion data of said subject and/or said imaging unit, a processing unit for extracting vital signs of said subject from said image data, and a control unit for adapting parameters of said imaging unit and/or said processing unit based on the received motion data.

In a further aspect of the present invention, a fitness device is presented that comprises the aforementioned device for monitoring vital signs of a subject and a motion detection unit for providing said device for monitoring vital signs with motion data of the subject and/or the imaging unit.

In yet another aspect of the present invention, there is provided a computer program which comprises program code means for causing a computer to perform the steps of the processing method when said computer program is carried out on a computer.

Preferred embodiments of the invention are defined in the dependent claims. It shall be understood that the claimed method, fitness device, and computer program have similar and/or identical preferred embodiments as the claimed device and as defined in the dependent claims.

Typical fields of application for monitoring vital signs are fitness devices. Exercises carried out on fitness devices typically comprise a substantially regular motion. This motion data can be used as an input to a device for monitoring vital signs of a subject. In this way, the cost of resources required for reliable vital signs monitoring (e.g. processing power, camera hardware) can be reduced and the reliability of detection can be increased compared to methods which are based on video analysis only. Hence, in an embodiment of the present invention, the interface of said device for monitoring vital signs can be configured to receive motion data of the subject from a fitness device.

A fitness device providing said motion data shall be understood in a broad sense. Conventional fitness devices include treadmills, exercise bikes, elliptical trainers, rowing machines, workout machines, weight lifting and weight lifting stations and the like. A motion detection unit in this context can be a sensor of said fitness device. Fitness devices shall also be understood with respect to new generation fitness devices, such as game consoles, TV sets or media programs that animate a subject to exercise, play or dance.

In a further embodiment, said motion data includes at least one type of a motion, a motion direction, a motion path, motion amplitude, a motion frequency, motion intensity, a resistance of force the subject has to work against, or anticipated motion characteristics. An exercise bicycle for example measures the revolutions per minute (RPM) which corresponds to a motion frequency. Moreover, said motion data can include physical and/or workout information about the subject whose vital signs are to be measured. Examples for said physical information are the body size of the subject, weight, body fat, age, skin type, body optical measurement, and also comprises information about the workout history or activity prior to exercising on said specific fitness device. Another aspect discloses a device for monitoring vital signs of a subject, wherein said control unit is configured to adapt the parameters of said processing unit to an expected value range for vital signs based on the received motion data. For example, if the user heavily exercises, a higher heart rate can be expected.

In a further aspect of the invention, the device for monitoring vital signs has a processing unit that is configured to determine the vital signs from a body part or a group of body parts, wherein said processing unit is configured to find and/or track said body part or group of body parts in said image data based on a received motion data. This reduces the amount of signal processing required. Instead of analyzing the entire image, only a region of interest (ROI) is evaluated. Hence, tracking the user from the video stream, for example by edge analysis of the single frames of the video stream which is very computational intensive, is not required. Instead, by knowing the movement of the user from the kind of exercise, for example a periodic left/right, left/right movement on an elliptical trainer, this movement can be anticipated and taken into account when calculating the vital signs information. Motion data, including frequency and amplitude of a movement, can be provided by sensors on the fitness device, measuring for example a stride rate or a resistance to work against. Further settings of the fitness device can be evaluated. External sensors can also provide motion data to the device for monitoring vital signs, for example a pedometer.

In a different embodiment, the control unit of said device for monitoring vital signs is configured to adapt at least one of the image acquisition rate, exposure time, focus, zoom or active sensing area of said imaging unit. The imaging unit can be a camera that adjusts its focus when the user is exercising, for example on a rowing machine, focusing to a close distance when the user is close to the imaging unit of the rowing machine, and focusing to a further distance if the user is further away. In a different example, the camera may increase its frame rate when the user is performing fast dancing moves, or reduce the image acquisition area to a limited dedicated area, for example when the user is on an exercise cycle when the user is rather stationary. Once again the device can use physical information about the subject. The location of the region of interest for evaluating vitals signs depends for example on the body size of the subject.

The processing unit of the device for monitoring vital signs may further comprise a filter for filtering said image data and/or vital signs, wherein the parameters of the filter depend on said motion data. It should be noted that filtering includes both pre-processing raw image data as well as post-processing extracted vital signs.

The control unit can further be configured to adapt the parameters of the processing unit for detecting frequency and/or amplitude components included in the received motion data, and correcting the image data and/or vital signs for said frequency and/or amplitude components. Frequency components in this context include both temporal and spatial frequencies in the motion data.

The processing unit of the vital signs monitor further comprises a filter for filtering said image data and/or vital signs, wherein the parameters of said filter depend on a derivative of said motion data. This option allows tracking vital signs data, for example when the intensity of a motion is rapidly increased. In this case the averaging time during measurement of said vital signs is reduced and the vital signs monitor is able to follow fast transients of vital signs. Along with the filter depending on the derivative of said motion data, the processing unit can be configured to determine a quality level indicating the reliability of said extracted vital signs depending on said motion data. If there is a fast transient, the averaging time can be reduced, so that the vital signs monitor is able to follow fast changes in vital signs information, which in turn may reduce the stability of the extracted vital signs.

Still further, in an embodiment said interface is configured to receive said motion data of said imaging unit from said imaging unit or a motion detection unit. As the motion of the imaging unit may also lead to considerable artifacts in the vital signs measurements, the motion of the imaging unit may be detected. This may be enabled by the imaging unit itself, e.g. by use of accelerometers within the imaging unit. Another option for detecting motion of the imaging unit is to use optical measurement means that are arranged at a fixed position within the room. By use of these motion data the vitals signs measurement can be corrected and, hence, made more accurate.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
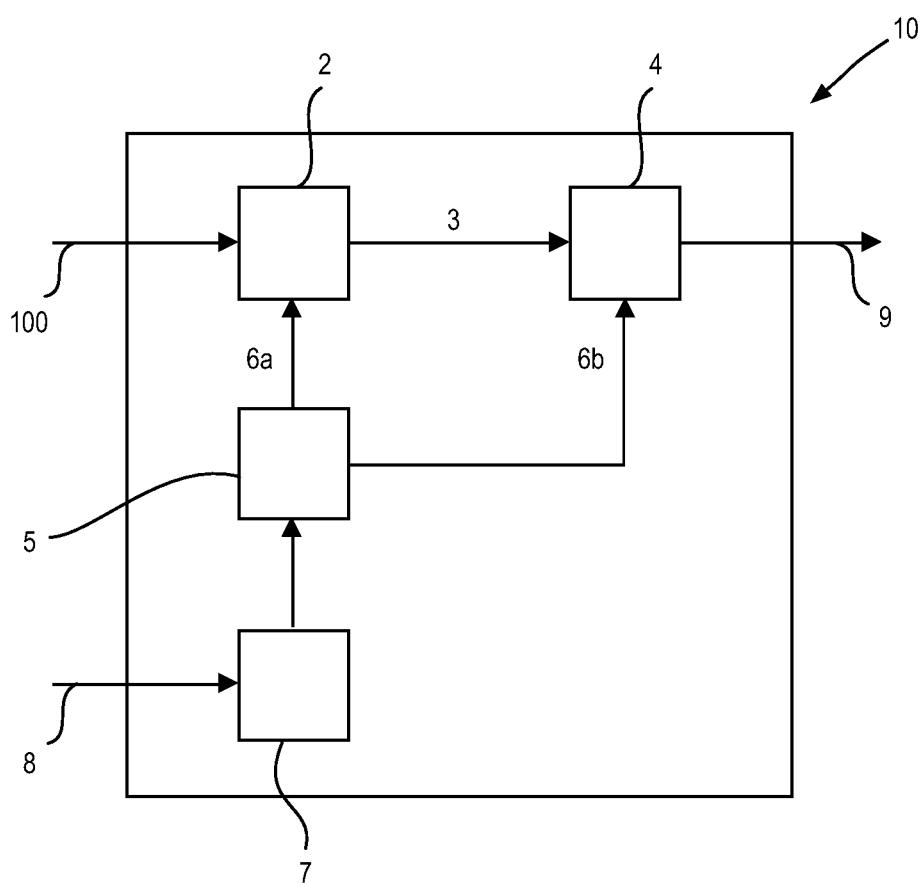
FIG. 1 shows a block diagram of a device for monitoring vital signs of a subject according to the present invention.

A device for monitoring vital signs of a subject according to the present invention is illustrated by way of an example in the block diagram shown in FIG. 1. Photoplethysmographic imaging is based on the principle that temporal variations in blood volume under the skin lead to variations in light absorption by the skin. Such variations can be detected and measured by taking images of an area of the skin and calculating the pixel average over a selected region. The average value over one or more pixels can be analyzed in frequency domain to extract periodic variations. Variations can also be detected by illuminating a selected area of skin with light and measuring the intensity of reflected light with a photosensor. In the example used herein, the device of FIG. 1 is arranged to determine the heart rate and respiratory frequency of the subject as the vital signs 9 of interest. However, the device can also be used to characterize the phase and/or frequency of other periodic biological phenomena e.g. the blood oxygenation level.

In the illustrated embodiment, the device for monitoring vital signs 1 includes an imaging unit 2, a processing unit 4, a control unit 5 and an interface 7 for receiving motion data 8.

The imaging unit 2 is configured to capture light 100 coming from a subject. The imaging unit can be any type of photodetector including a standard of the shelf video camera that supplies image data 3 to the processing unit 4. This image data 3 is analyzed by the processing unit 4 to extract periodic biological phenomena, in general vital signs, such as heart rate or respiratory frequency. This process including the components imaging unit 2 and processing unit 4 for extracting vital signs 9 is generally known in the art and will not be described in more detail. The basic principle is e.g. described in the paper by Schmitz "Video Camera based Photoplethysmography using Ambient Light" (Graduation Symposium at the Technical University of Eindhoven, 2011).

In addition to the aforementioned components already known in prior art photoplethysmography imaging systems, the device for monitoring vital signs according to the present invention includes an interface 7 for receiving motion data 8 of the subject and/or of the imaging unit 2 and a control unit 5 for adjusting parameters 6a of the imaging unit 2 and/or adjusting parameters 6b of the processing unit 4.

Figure 2A:
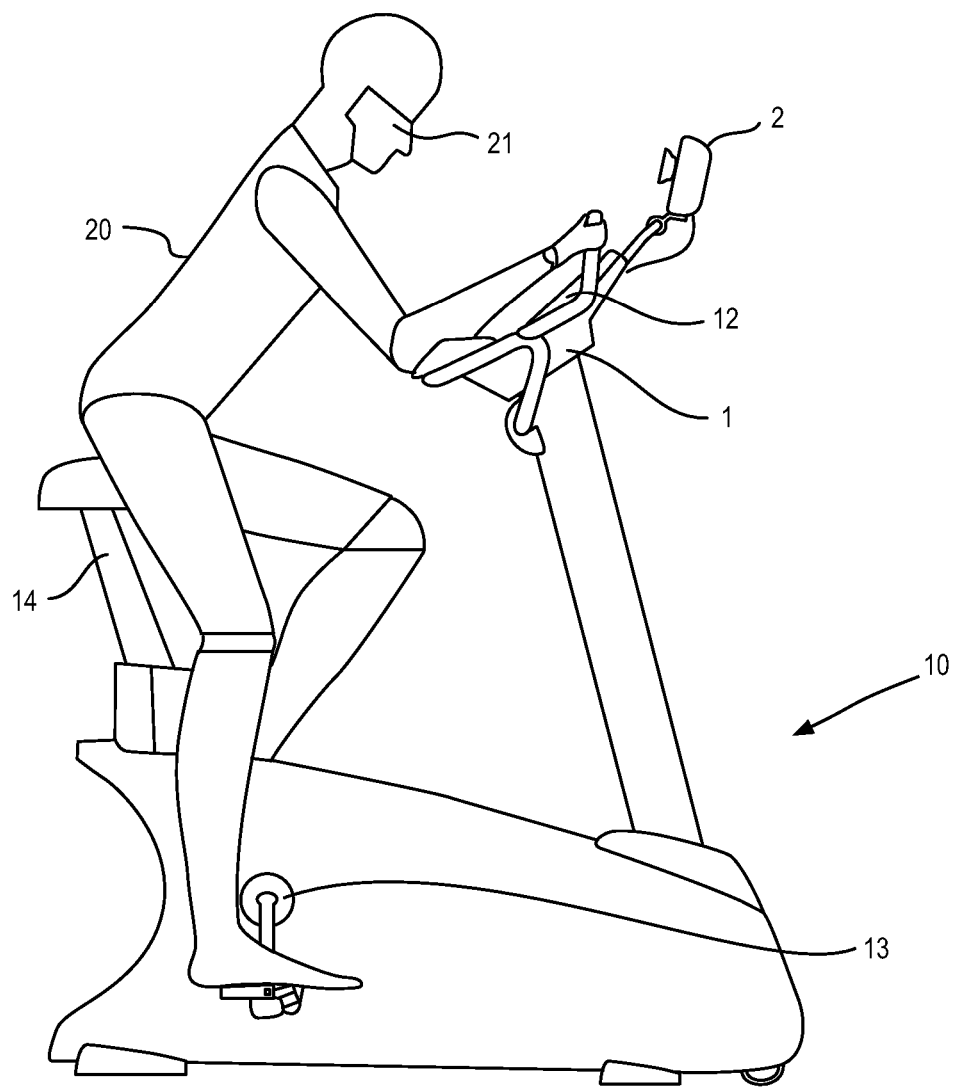
FIG. 2A shows a first embodiment of a fitness device according to the present invention.

An embodiment of the fitness device according to the present invention is shown in FIG. 2A including a device for monitoring vital signs 1. The fitness device 10 in this example is an exercise bicycle for the user 20 to work out. Conventional systems for measuring vital signs of the subject during workout require the user to be in direct contact with a sensing unit, for example by wearing a chest-strap that directly measures the heart rate or hold on to specific contact based sensors of the fitness device 10. Wearing such a chest-strap or being required to hold on to a specific location of the fitness device is inconvenient for the user. Moreover a given sensor location forces the user into specific positions during his workout.

Still further, a fitness exercise on a device equipped with the proposed imaging unit 2 might cause artifacts of vital signs measurements not only due to motion of the body of the user, but also due to a motion of the imaging device 2. Depending on the configuration of the fitness device, type of exercise, and location of the imaging device 2, the motion of the imaging device 2 might be even more severe (and more damaging for the stability of vital signs measurements) than a motion of the user. This is dealt with according to an embodiment of the present invention by detecting motion data of the imaging unit 2 and using these motion data for adapting parameters of said imaging unit 2 and/or said processing unit 4.

The device for monitoring vital signs 1 according to the present invention overcomes these limitations. The fitness device 10 is equipped with an imaging unit 2 that faces the subject 20. More specifically the imaging unit 2 is directed towards and/or tracks an area of bare skin 21 from which temporal variations of the color of the skin can be extracted. Besides these temporal variations of the color of the skin because of the vital signs to be measured, the user also performs a periodic movement that depends on exercise to be carried out on said fitness device 10. In the example of an exercise bicycle depicted in FIG. 2A, the user performs a pedaling movement with his legs which also influences the movement of the upper body. This movement of the upper body can cause motion artifacts that are also present in the image data 3, which in turn is further processed by the processing unit 4 to extract vital signs 9. Motion artifacts due to exercises may fall into a frequency range that is also common for vital sign parameters. For example a cycling frequency of 100 strides per minute may well be interpreted as a heart rate, the latter ranging typically from about 60 beats per minute to 180 beats per minute.

This fitness device 10 according to the present invention also comprises a motion detection unit 13 for providing the device for monitoring vital signs 1 with motion data 8. In this exemplary embodiment of a fitness device, the motion detection unit 13 is a sensor that measures the revolutions per minute (RPM). Assuming that 100 revolutions per minute are measured, this at least one component of motion data 8 is fed via an interface 7 to the control unit 5. The image data 3 from the imaging unit 2 contains at least both the frequency components from the vital sign data as well as frequency components from the motion data. As a frequency component of the motion data is readily available from the RPM sensor, the control unit 5 can feed a second parameter 6b to the processing unit 4 which in turn allows for correction of vital signs in terms of frequency components included in the motion data. This will be exemplarily described in more detail with reference to FIG. 3.

Instead of or in addition to adapting a parameter 6b of the processing unit 4, motion data 8 can also be used to adapt a parameter 6a of the imaging unit 2. If a fast motion frequency is detected, the image acquisition rate of the imaging unit, e.g. the frame rate of a video camera serving as the imaging unit is adjusted such that said frame rate is well suited to capture a frequency corresponding to the primary components of the motion data.

In another embodiment of the present invention, the motion detection unit measures a configuration of the fitness device 10 on which a motion shall be performed. A height sensor 14 for measuring the height of the saddle of the exercise bicycle in FIG. 2A can supply this height as an input 8 to the device for monitoring vital signs 1. This height information received via the interface 7 is used by the control unit 5 to set a parameter 6a of the imaging unit 2. Said parameter 6a configures the imaging unit 2 to evaluate a specific pixel area related to said height. For example if the saddle is set to a high position, a tall user can be anticipated and hence the face or area of bare skin 21 for extraction of vital signs is most likely located in an upper part of images in the image data 3 acquired by the imaging unit 2.

Depending on the type of fitness device, other parameters of the imaging unit 2 or processing unit 4 may be adjusted, for example the camera focus on a rowing machine where the distance of the subject with respect to the imaging unit 2 changes periodically. In the example of a rowing machine also the number of evaluated pixels can be varied periodically, because the size of an image of a region of interest for extracting vital signs, e.g. an area of bare skin 21, changes. The motion data in this context may comprise sensor data corresponding to the position of the user with respect to the imaging unit 2 or simply determine the type of fitness device. Said motion data 8 describing the type of fitness device provides information to the processing unit 4 about an anticipated movement of the user (e.g. left-right or up-down movement) that can be taken into account for compensation of motion artifacts when calculating vital signs.

Figure 2B:
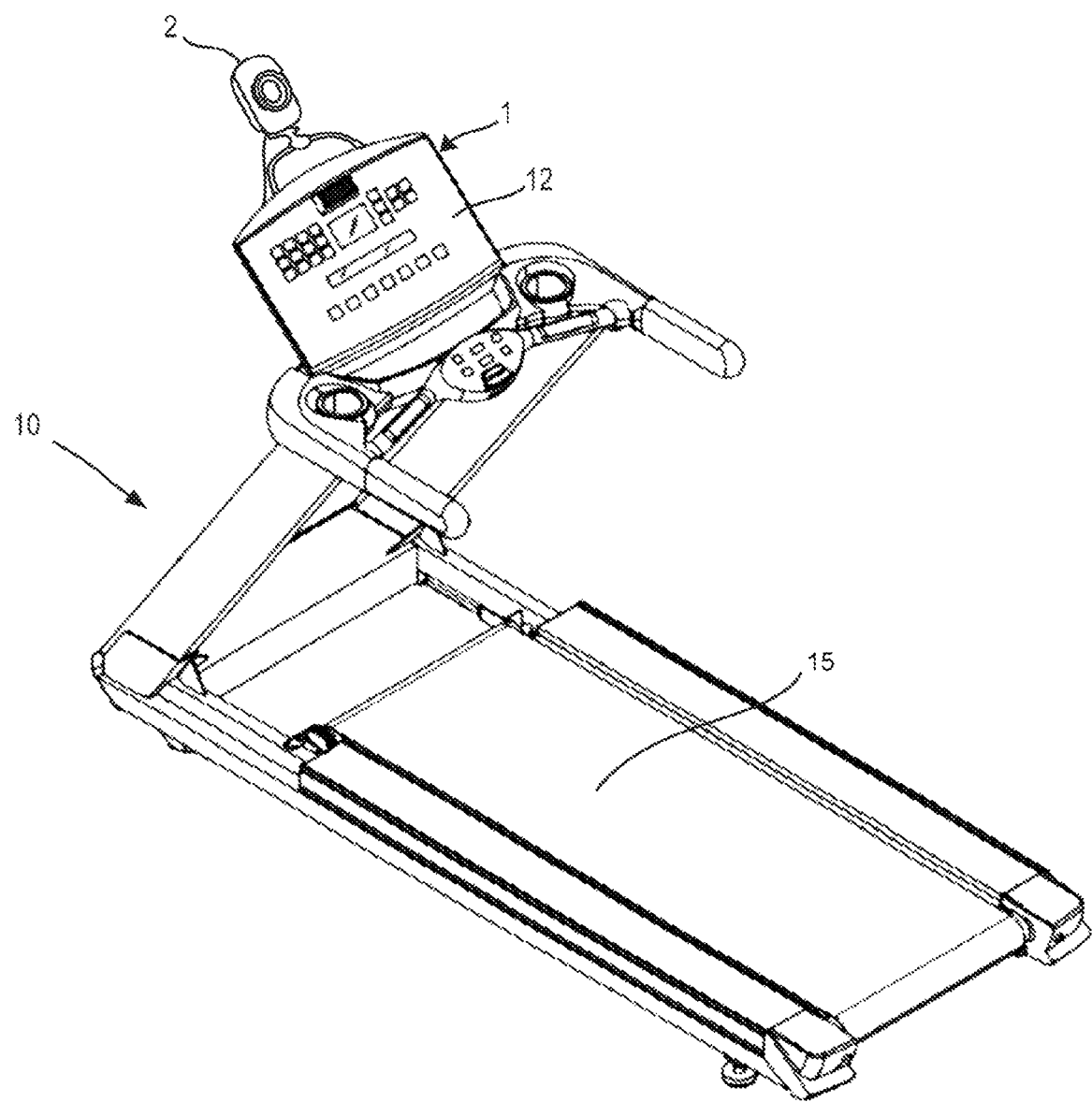
FIG. 2B shows a second embodiment of the fitness device according to the present invention.

FIG. 2B discloses a further embodiment of the fitness device 10 according to the present invention including a device for monitoring vital signs 1 of the subject 20 according to the present invention. The fitness device 10 in FIG. 2B is a treadmill. In addition to treadmills according to prior art the treadmill 10 according to the present invention also includes an imaging unit 2 as a part of the device for monitoring vital signs 1. A user interface 12 generally has a double functionality: first to provide the user with information about his workout and vital signs and second to provide an input for entering physiological or workout information as motion data 8. This physical information includes for example body size, weight and age which can be used to estimate a probable value range for vital signs. For an elderly person it is less likely to reach a heart rate of 180 beats per minute than for a kid. The treadmill 10 in this example may additionally be equipped with a stride sensor 15 to provide sensory motion data 8. In an alternative embodiment said motion data 8 for further processing in the device for monitoring vital signs can be supplied from additional external sensing units, e.g. the acceleration sensor in a smart phone or audio player. Especially non-sensory motion data 8, such as the work-out history or physiological parameters can be provided from a database or online source through an interface 7.

It shall be noted that elements shown only in one of the embodiments of FIGS. 2A and 2B may also be provided in the other embodiment, or, more generally, in other embodiments of fitness devices.

FIG. 3 shows a simplified sketch of periodic signals included in the image data in frequency domain.

Figure 3A:
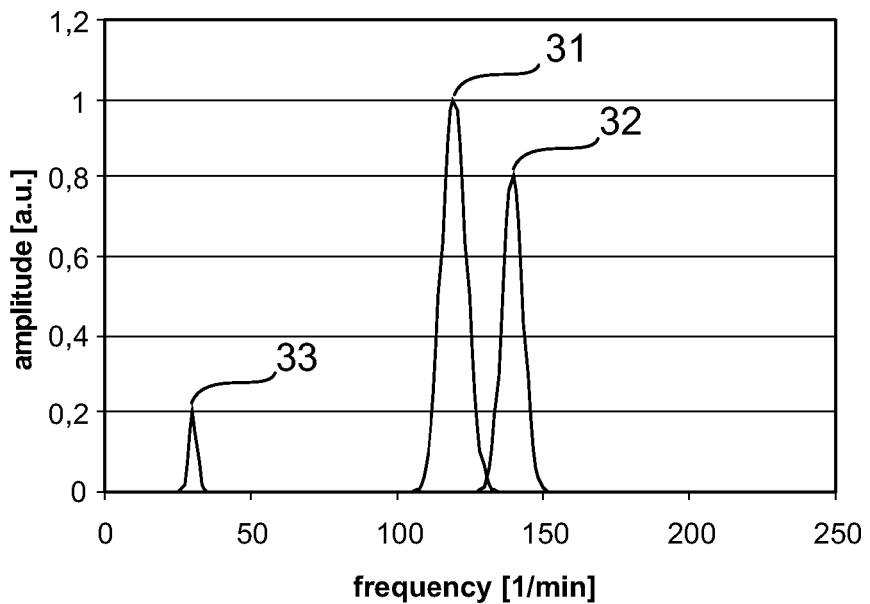
FIG. 3A shows a spectrogram of the extracted vital signs according to prior art.
Figure 3B:
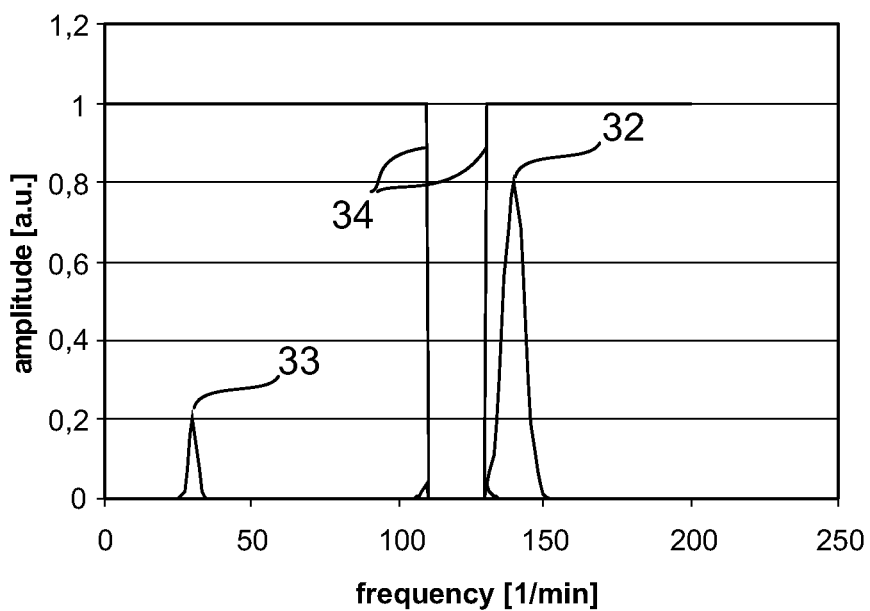
FIG. 3B shows a spectrogram of the extracted vital signs according to the present invention after postprocessing.

FIG. 3A shows a simplified graph of image data in frequency domain according to prior art that includes three main peaks. Frequency peak 31 is centered at 120 l/min, frequency peak 32 is centered at 140 l/min and frequency peak 33 is centered at 30 l/min. If the processing unit now tries to extract the dominant frequency it would certainly select frequency peak 31 at 120 l/min, which is also well within the expected value range for a heart rate. However, the same holds true for frequency peak 32 at 140 l/min. While the known system according to prior art is capable of identifying both frequency peaks it is not able to distinguish which of the two is a motion artifact and which is the actual heart rate to be measured. The frequency peak 33 at 30 l/min can clearly be identified as a respiratory frequency as it is too low to be a heart rate.

The device for monitoring vital signs 1 according to the present invention overcomes this limitation by including information from motion data 8. A motion detection unit 13 from a fitness device 10, for example the RPM sensor from FIG. 2A, supplies the control unit 5 with this motion data 8 via an interface 7 and feeds the RPM value as parameter 6a onto the processing unit 4. If the sensor now detected 120 RPM, the processing unit can apply a filter to the frequency spectrum extracted from the image data 3. Said filter can be any type of filter which reduces frequency components from the motion data. A simple example is a band stop filter with an amplitude transfer function 34 as sketched in FIG. 3B. The resulting spectrum after filtering now has two frequency peaks 32 and 33 which can clearly be identified as the heart rate and the respiratory frequency.

The aforementioned signal processing and filtering can be considered as a type of postprocessing as it is applied to the spectrum already extracted from the image data. However, the use of motion data is not limited to postprocessing but can also be applied to raw image data coming from the imaging unit.

Figure 4A:
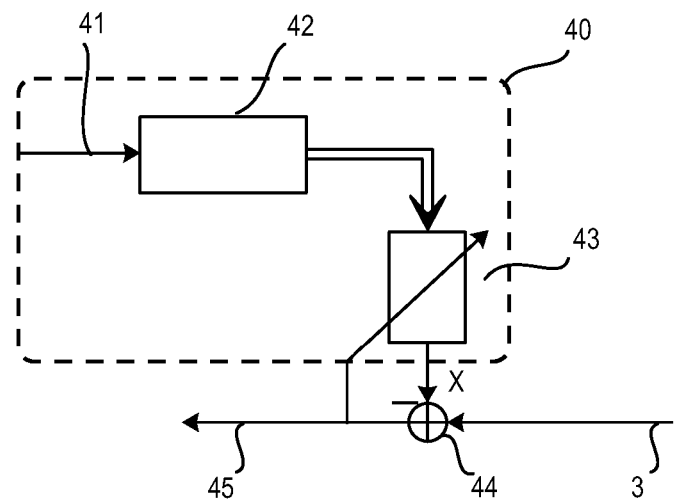
FIG. 4A shows a filter configuration according to the present invention.

FIG. 4A presents an exemplary filter configuration 40. In a first step (not shown) a motion frequency 41 is extracted from the motion data 8. This motion frequency 41 is fed into a quadrature oscillator 42 to extract its real and imaginary part. These signals are then fed to an adaptive filter 43, the output of which is then subtracted from image data or camera signal 3 from the imaging unit 2 in mixer 44. The output signal 44 is now the difference of the signal from the adaptive filter x and image data 3. Parameters of the adaptive filter can be chosen such that the output signal has same amplitude and phase as a periodic component due to motion artifacts in the camera signal 3. This can for example be achieved with a feedback path from the output signal 45 to the adaptive filter 44. Hence, the two signals cancel out and the respective motion artifact is not present in the output signal 44 anymore.

Figure 4B:
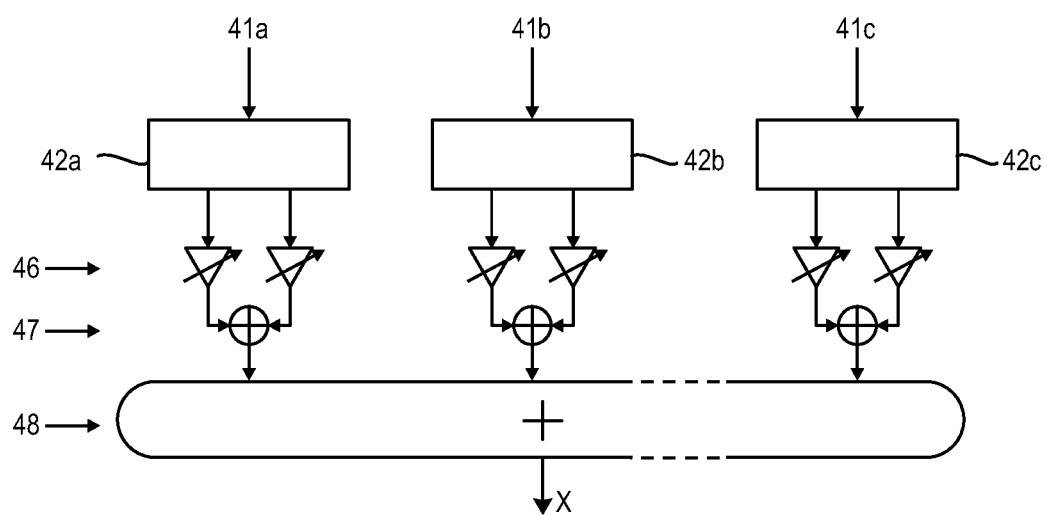
FIG. 4B shows another filter configuration according to the present invention in more detail.

FIG. 4B shows a more detailed embodiment of an adaptive filter which is not limited to one motion frequency but can correct for a multitude of motion frequencies 41a to 41c. For each frequency channel 41a to 41c there is a separate quadrature oscillator 42a to 42c with phase and amplitude adjustment stages 46, the two quadrature components at each frequency being then combined in stage 47 and further combining the signals of all frequency channels in step 48. The output signal x of step 48 is then subtracted from the image data 3 as already shown in FIG. 4A.

In a further embodiment the control unit 5 and/or processing unit consider not only the present value of motion data 8, but also a rate of change or a derivative of at least components of said motion data 8. Filter parameters can be adjusted dependent on this rate of change. Once again referring to the fitness device 10 from FIG. 2A, the exercise bicycle may provide workout profiles, e.g. changing the resistance a user has to work against over time. When the resistance is constant over a period of time e.g. several minutes, the heart rate and/or respiratory frequency of the subject reach a rather stable value. Hence, the processing unit 4 can be adjusted to average an extracted heart rate over a longer interval and provide a rather stable vital sign output value 9. This can be indicated by a reliability parameter or quality level of said vital signs 9. On the other hand if the resistance of the exercise bicycle quickly changes, the heart rate has to be tracked with fine timing resolution. Thus, the time interval for averaging has to be reduced. Hence, the measured heart rate may be less reliable, which in turn can be represented by said quality level of the vital signs 9.

Once again it should be highlighted that motion data, for example the frequency components of the motion of the subject are provided through an interface for receiving motion data of said subject and do not have to be extracted from the image data for example by means of edge detection which in turn requires computational intensive signal processing and the respective costly hardware to cope with image processing algorithms.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for monitoring vital signs of a subject, comprising:
    an imaging unit for remotely obtaining image data of said subject,
    an interface for receiving motion data of said subject, wherein said interface is configured to receive said motion data of said subject from a fitness device, the motion data from the fitness device not being based on video analysis, processing circuitry for extracting vital signs of said subject from said image data, and control circuitry for adapting parameters of said imaging unit or said processing circuitry based on the received motion data to compensate for artifacts of motion in the image data.

2. The device according to claim 1, wherein said motion data includes at least one of a type of motion, a motion direction, a motion path, a motion amplitude, a motion frequency, a motion intensity, a resistance and force the subject has to work against.

3. The device according to claim 1, wherein said motion data includes physical or workout information about the subject whose vital signs are to be measured.

4. The device according to claim 1, wherein said control circuitry is configured to adapt the parameters of said processing circuitry to an expected value range for vital signs based on the received motion data.

5. The device according to claim 1, wherein said processing circuitry is configured to determine the vital signs from a body part or group of body parts, wherein said processing circuitry is configured to find or track said body part or group of body parts in said image data based on the received motion data.

6. The device according to claim 1, wherein said control circuitry is configured to adapt at least one of the image acquisition rate, exposure time, focus, zoom and active sensing area of said imaging unit.

7. The device according to claim 1, wherein the processing circuitry comprises a filter for filtering said image data or vital signs, wherein the parameters of said filter depend on said motion data.

8. The device according to claim 1, wherein the control circuitry is configured to adapt the parameters of the processing circuitry for
detecting frequency or amplitude components included in the received motion data, and
correcting the image data or vital signs for said frequency or amplitude components.

9. The device according to claim 1, wherein the processing circuitry comprises a filter for filtering said image data or vital signs, wherein parameters of said filter depend on the derivative of said motion data.

10. The device according to claim 1, wherein the processing circuitry is configured to determine a quality level indicating the reliability of said extracted vital signs depending on said motion data.

11. The device according to claim 1, wherein said interface is configured to receive said motion data of said imaging unit from a motion detection unit.

12. A fitness device, comprising: a device for monitoring vital signs of a subject comprising: an imaging unit for remotely obtaining image data of said subject; an interface for receiving motion data of said subject, wherein said interface is configured to receive said motion data of said subject from a fitness device, the motion data from the fitness device not being based on video analysis; processing circuitry for extracting vital signs of said subject from said image data; and control circuitry for adapting parameters of said imaging unit or said processing circuitry based on the received motion data to compensate for artifacts of motion in the image data; and a motion detection unit for providing said device for monitoring vital signs with motion data of the subject.

13. A method for monitoring vital signs of a subject, comprising: remotely obtaining, by processing circuitry, image data of said subject from an imaging unit; receiving motion data of said subject at the processing circuitry, wherein said motion data of said subject is received from a fitness device, the motion data from the fitness device not being based on video analysis; extracting vital signs of said subject from said image data using the processing circuitry; and adapting parameters of the imaging unit or adapting parameters of the processing circuitry based on the received motion data to compensate for artifacts of motion in the image data.

14. A non-transitory computer readable medium having a computer program embodied thereon for causing a processor, when executing the computer program, to carry out a method for monitoring vital signs of a subject, the method comprising: remotely obtaining image data of said subject from an imaging unit; receiving motion data of said subject, wherein said motion data of said subject is received from a fitness device, the motion data from the fitness device not being based on video analysis; extracting vital signs of said subject from said image data using processing circuitry; and adapting parameters of the imaging unit or adapting parameters of the processing circuitry based on the received motion data to compensate for artifacts of motion in the image data.

15. The device according to claim 1, wherein the received motion data is a number of revolutions per minute of a component of the fitness device.

16. The device according to claim 15, wherein the fitness device comprises pedals and the received motion data is a number of revolutions per minute of the pedals.

17. The device according to claim 11, wherein the motion detection unit is a stride sensor.

\* \* \* \* \*